United States Patent
Miura et al.

(10) Patent No.: US 8,158,403 B2
(45) Date of Patent: Apr. 17, 2012

(54) ENHANCER OF PROLIFERATION OF LACTIC ACID BACTERIUM, AND AGENT FOR IMPROVEMENT IN SURVIVABILITY OF LACTIC ACID BACTERIUM

(75) Inventors: Mari Miura, Saitama (JP); Yasuyuki Seto, Saitama (JP); Masayuki Watanabe, Saitama (JP); Toshimitsu Yoshioka, Saitama (JP)

(73) Assignee: Megmilk Snow Brand Co., Ltd., Sapporo (JP)

( * ) Notice: Subject to any disclaimer, the term of this patent is extended or adjusted under 35 U.S.C. 154(b) by 504 days.

(21) Appl. No.: 12/306,975

(22) PCT Filed: Jun. 26, 2007

(86) PCT No.: PCT/JP2007/000694
§ 371 (c)(1),
(2), (4) Date: Feb. 19, 2009

(87) PCT Pub. No.: WO2008/001497
PCT Pub. Date: Jan. 3, 2008

(65) Prior Publication Data
US 2009/0317892 A1 Dec. 24, 2009

(30) Foreign Application Priority Data
Jun. 30, 2006 (JP) .................... 2006-182374

(51) Int. Cl.
*A23C 9/12* (2006.01)
*C12N 1/20* (2006.01)
*C12N 1/38* (2006.01)
(52) U.S. Cl. ............... 435/252.9; 435/253.4; 435/244; 426/34; 426/36
(58) Field of Classification Search .............. None
See application file for complete search history.

(56) References Cited

U.S. PATENT DOCUMENTS

| 2005/0180962 A1* | 8/2005 | Raz et al. ............ 424/93.45 |
| 2009/0035288 A1* | 2/2009 | Albers et al. ......... 424/93.45 |

FOREIGN PATENT DOCUMENTS

| JP | 03-120222 | 5/1991 |
| JP | 05-252900 | 10/1993 |
| JP | 2001-275658 | 10/2001 |
| JP | 2001-278794 | 10/2001 |
| JP | 2005-021156 | 1/2005 |
| WO | 01/95741 | 12/2001 |
| WO | 2005/058335 | 6/2005 |

OTHER PUBLICATIONS

P. Arne Hansen, A Study in Cheese Ripening. The Influence of Autolyzed cells of *Streptococcus cremoris* and *Streptococcus lactis* on the Development of *Lactobacillus casei*. J Dairy Sci. (1941) vol. 24, No. 11, p. 969-976.
"Evaluation of lactic acid bacteria autolysate for the supplementation of lactic acid bacteria fermentation" World Journal of Microbiology and Biotechnology, vol. 16, No. 2, Mar. 2000, pp. 207-209, XP002580929.
European Patent Office issued an European Search Report dated May 21, 2010, Application No. 07790217.9.

* cited by examiner

*Primary Examiner* — S. Devi
(74) *Attorney, Agent, or Firm* — Young & Thompson

(57) ABSTRACT

A dead cell of a lactic acid bacterium or a culture containing the dead cell of a lactic acid bacterium is added to the dairy products such as yogurt, cheese, milk beverage or the like in an amount of 0.001 wt % or more in dry weight of the dead cell, therefore, it is possible to enhance the growth of a lactic acid bacterium, to shorten the time required for fermentation, and to improve the viability of a lactic acid bacterium during storage over a long period, without affecting the flavor or production cost of the dairy product.

6 Claims, 4 Drawing Sheets

ENHANCER OF PROLIFERATION OF LACTIC ACID BACTERIUM, AND AGENT FOR IMPROVEMENT IN SURVIVABILITY OF LACTIC ACID BACTERIUM

TECHNICAL FIELD

The present invention relates to an agent for enhancing growth and improving viability of a lactic acid bacterium.

BACKGROUND ART

Various physiological effects of lactic acid bacteria, such as intestinal regulation effect, defense against infection, immunostimulatory action, and cancer prevention, have been found one after another, and developments have been made for using lactic acid bacteria or cultures thereof as materials for health foods, drugs, or the like. Moreover, recent studies have reported that the above-mentioned functions can be improved by delivering the lactic acid bacteria in a viable condition to intestines, and improvement of the viability in the product has a great industrial advantage in applications to Foods for Specified Health Use (FOSHU) rapidly increasing the demand for the foods in recent years.

However, the viability of a lactic acid bacterium is affected depending on the bacterial strain, culture phase, product pH, or concentration of sugar used as a sweetener, and it is very difficult to improve the viability of the lactic acid bacterium while keeping the original taste of the product. Therefore, special containers are used in order to suppress oxygen permeation as much as possible, but the containers have a problem of increase in the cost. Moreover, as a method of producing a low-fat yogurt causing little decrease in a lactic acid bacterium during storage, a method of improving the survival rate of the lactic acid bacterium by adding oleic acid, or a salt or ester thereof to a fermentation medium has been disclosed (for example, see Patent Document 1). However, most of oleic acid-related compounds that may be used as food additives in Japan have distinctive smells, and use of the compounds inevitably results in deterioration of the flavor of the products. Even though the viability is improved while deteriorating the flavor, the survival rate is as low as 40%.

Furthermore, a method of producing a liquid yogurt with low viscosity and high viability by adding peroxidase to a raw material mixture has been disclosed (for example, see Patent Document 2), but there is a problem that addition of such material may affect the cost of the product.

On the other hand, in order to exert physiological effects of a lactic acid bacterium, it is important to maintain a larger number of viable cells in the product. However, to increase the number of viable cells, it is necessary to take longer culture time, resulting in deterioration of productivity. A method of promoting the growth of lactic acid bacteria to increase the bacterial cell concentration and to shorten the culture time enables simple and inexpensive production of a culture of lactic acid bacteria and is highly significant from the industrial viewpoint.

Various attempts have been made as methods of promoting growth of lactic acid bacteria. For example, there have been disclosed Euglena cell and/or an extract thereof (for example, see Patent Document 3), a product obtained by removing high-molecular materials from a cucumber extract (for example, see Patent Document 4), a degradation product obtained by treating whey protein with protease (for example, see Patent Document 5), sake lees (for example, see Patent Document 6), a purified pyroligneous acid solution (for example, see Patent Document 7) and the like. Addition of such substances may affect the flavor of the product and raise a problem of an increase in the cost due to complex and cumbersome processes in preparation or purification of the materials.

Patent Document 1: JP-A-2001-45968
Patent Document 2: JP-A-H10-262550
Patent Document 3: JP-A-H07-99967
Patent Document 4: JP-A-2000-41655
Patent Document 5: JP-A-2004-57047
Patent Document 6: JP-A-2005-151927
Patent Document 7: JP-A-2005-318856

DISCLOSURE OF THE INVENTION

Problems to be Solved by the Invention

A material having the effect of enhancing growth of a lactic acid bacterium which is obtained using a conventional technology, had problems such as a complex and cumbersome process in preparation, expensive material itself, and in order to prevent specific taste or odor from transferring to commercial products in producing the products, only a very small amount of the material could be added to a medium so that the flavor of the products is not affected. In consideration of such problems, an object of the present invention is to provide a novel agent for enhancing growth and improving viability of a lactic acid bacterium, which has an excellent ability to enhance growth of the lactic acid bacterium and improve viability of the lactic acid bacterium in the product, has no adverse effect on the flavor of the product, and has low production cost.

Means for Solving the Problems

The inventors of the present invention have made extensive studies to obtain an agent for enhancing growth and improving viability of a lactic acid bacterium, which has an excellent ability to enhance growth and improve viability of the lactic acid bacterium and has no adverse effect on the flavor and the production cost thereof. As a result, the inventors have found that a dead cell of a lactic acid bacterium or a culture containing the dead cell has the effect of remarkably improving the viability of a lactic acid bacterium. Moreover, the inventors have also found that the dead cell of a lactic acid bacterium or the culture containing the dead cell has the effect of enhancing growth of a lactic acid bacterium which is object to be grown. That is, the inventors have found that use of the dead cell of a lactic acid bacterium or the culture containing the dead cell is effective to enhance growth of a lactic acid bacterium to be grown and to maintain the high number of viable cells in the product without impairing the flavor of the product and while preventing increase in the cost due to use of a special and expensive container which suppressing oxygen transmission as much as possible, thereby completing the present invention. That is, the present invention provides an agent for enhancing growth and improving viability of a lactic acid bacterium, which contains a dead cell of a lactic acid bacterium or a culture containing the dead cell as an active ingredient.

Effect of the Invention

An agent for enhancing growth and improving viability of a lactic acid bacterium, which has the effect of remarkably enhancing growth of a lactic acid bacterium to be grown and also maintaining the high number of viable cells in the product, can be produced by added the dead cell of a lactic acid bacterium or the culture containing the dead cell during culturing a lactic acid bacterium to be grown without impairing the flavor of the product and while preventing increase in the cost due to use of a special and expensive container for suppressing oxygen transmission as much as possible.

BEST MODE FOR CARRYING OUT THE INVENTION

In the present invention, the dead cell of a lactic acid bacterium may be prepared by: sterilizing a medium where the lactic acid bacterium has been cultured and collecting the dead cell by filtration, centrifugation or the like, followed by concentrating and drying as required. Alternatively, the dead cell may also be prepared by collecting the cultured cell and then sterilizing the cell, followed by concentrating and drying as required.

In the present invention, the culture containing the dead cell of a lactic acid bacteria may be prepared by: sterilizing a medium, as it is, where the lactic acid bacterium has been cultured, followed by concentration or drying as required. Alternatively, the culture may also be prepared by filtering or centrifuging the medium where the lactic acid bacterium has been cultured to increase the concentration of the cell and then sterilizing the resultant cell, followed by concentration or drying as required.

In the present invention, the culture substrate containing the dead cell of a lactic acid bacteria may be prepared as a medium, material component, or composition, which is newly composed by adding a dead cell of a lactic acid bacterium or a culture containing the dead cell and supplementing with a nutritional source necessary for culture of microorganisms.

The sterilization includes not only heating but also a conventional method of killing a bacterium, such as UV or γ-ray irradiation.

The agent for enhancing growth and improving viability of a lactic acid bacterium of the present invention is used as an aqueous solution as is or used in the state of a concentrated solution or powder as described above. The acidic buttermilk obtained in production of fermented butter produced by fermentation using a lactic acid bacterium can be used in the state of a concentrated solution or powder containing the dead cell of the lactic acid bacterium. The material containing a cell of a lactic acid bacterium which was used as a starter may also be used as well as a culture. A material containing a dead cell of a lactic acid bacterium used as a starter such as cheese whey which is obtained in production of cheese produced by fermentation using a lactic acid bacterium may also be used as well as a culture containing a dead cell of a lactic acid bacterium. The bacterial cell and culture are, as required, subjected to concentration or drying, during which a dead cell may be obtained by providing a sterilization step.

The agent for enhancing growth and improving viability of a lactic acid bacterium containing a dead cell of a lactic acid bacterium, a culture containing the dead cell, or an acidic buttermilk containing the dead cell as an active ingredient may be used as is, or may be prepared a new constitution as a culture substrate such as a medium, material component, or composition supplementing with a nutritional source necessary for culture of microorganisms by adding to another nutritional component. The agent for enhancing growth and improving viability of a lactic acid bacterium containing a dead cell of a lactic acid bacterium, a culture containing the dead cell, or an acidic buttermilk containing the dead cell as an active ingredient may be prepared concentrated milk or powdered milk by adding to milk or skim milk and concentrating or drying, as required. In addition, the agent may be used by powder/powder mixing with plural powdered milk products.

The embodiments of the present invention may include: the agent for enhancing growth and improving viability of a lactic acid bacterium may be directly added as is to a fermentation mixture for a fermented milk product; and the agent for enhancing growth and improving viability of a lactic acid bacterium may be used by adding to a seed or bulk starter of the lactic acid bacterium to be grown.

In fermentation for an intended product, the dead cell obtained as above may be directly added to a fermentation mixture, the mixture is sterilized, and a starter of a lactic acid bacterium is added to the sterilized mixture to start fermentation, thereby preparing a fermented milk product; or the dead cell obtained as above may be added to a skim milk medium that is conventionally used in culture of a lactic acid bacterium, the mixture is sterilized, a lactic acid bacterium to be grown is inoculated into the mixture, culturing the bacterium to prepare a seed or bulk starter, after that, the resultant seed or bulk starter is added to the sterilized fermentation mixture to start fermentation, thereby preparing a fermented milk product.

The effects can be achieved by causing a bacterial cell serving as an agent for enhancing growth and improving viability of a lactic acid bacterium to contain at a concentration of 0.001 wt % or more per solid content.

The lactic acid bacterium used as the dead cell of the present invention includes rod-shaped lactic acid bacteria such as the genus of *Lactobacillus* and *Weissella*, round-shaped lactic acid bacteria such as the genus of *Pediococcus, Leuconostoc, Lactococcus, Streptococcus*, and *Enterococcus*. Any lactic acid bacterium is effective, and plural lactic acid bacteria may be used in combination. As lactic acid bacteria used for the purpose of enhancing growth and improving viability, any lactic acid bacterium that are commonly used in fermented dairy products, such as *Lactobacillus* and *Lactococcus*, can be used.

Whether the lactic acid bacterium used as the dead cell of the present invention and lactic acid bacterium to be enhanced the growth and improved the viability may be the same or different, the effects can be achieved in any case.

The results of a fermentation test reveal that a medium containing the dead cell of the present invention is remarkably excellent in fermentation ability of the lactic acid bacterium and remarkably improved in viability of the lactic acid bacterium during storage as compared with a general skim milk medium.

As described above, the growth of a lactic acid bacterium, acid production by a lactic acid bacterium, and viability of a lactic acid bacterium in the product may be easily improved by adding the bacterial cell of the present invention, and special containers is not required for limiting oxygen permeation as much as possible and it is not necessary to maintain pH around neutral. Therefore, the product can be produced in a short time without impairing the original flavor of the product while preventing increase in cost. There have been reported no cases in which the viability of a lactic acid bacterium is improved and the growth of a lactic acid bacterium is enhanced in product by using a dead cell of a bacterium.

Hereinafter, the present invention will be described in detail by way of Examples. However, the following Examples are intended to describe the present invention and the present invention is not limited to the description of the Examples.

Example 1

*Lactobacillus casei* ATCC334, *Lactobacillus acidophilus* JCM1132, *Lactobacillus helveticus* JCM1120, *Lactobacillus* plantarum NCFB1752, *Lactococcus lactis* subsp. *lactis* ATCC19435, *Leuconostoc mesenteroides* subsp. *mesenteroides* JCM6124, and *Pediococcus pentosaceus* JCM5890 were separately cultured in MRS broth (manufactured by Difco), and the bacterial cells were collected by centrifugation. Then, water was added to dilute the cells to the initial liquid volumes, and centrifugation was carried out again to collect the bacterial cells. The resultant washed cells were sterilized and then freeze-dried or spray-dried to prepare dead cell powders of the present invention.

The acid producing ability and viability tests were conducted using the dead cell powders. The dead cell powders were respectively added to a fermentation mixture (16% skim milk+7% isomerized sugar) so as to have concentration of 0.01%, and the mixtures were sterilized at 95° C. for 90 minutes. The fermentation mixture (16% skim milk+7% isomerized sugar) was used as a control (CTR). *Lactobacillus casei* ATCC334 was inoculated into each fermentation mixture at a concentration of 0.5%, after that the mixture was cultured at 37° C. until the acidity reached 2.1%. The cultures were mixed with isomerized sugar to produce yogurt drinks with BRIX of 15%. The yogurt drinks were stored at 15° C., and the cells of the lactic acid bacterium were counted on days 0, 7, 14, and 21. Moreover, for the purpose of comparison of the acid producing ability, the acidity during fermentation was determined with time 0, 24, 48, 72, and 96 hours after storage.

The effect of addition of the dead cells was shown in FIG. 1 on acid production by *Lactobacillus casei*, and in FIG. 2 on viability of *Lactobacillus casei*, respectively. The results reveal that, as shown in FIG. 1, acid production is improved in all the samples to which the dead cells were added. Furthermore, as shown in FIG. 2, changes in the numbers of bacterial cells during storage of the products show that viability is remarkably improved in all the samples to which the dead cells were added as compared with the control.

Example 2

Dead cell powders of the present invention were prepared in the same manner as described in Example 1.

The acid producing ability test and viability test were conducted using dead cell powders of *Lactobacillus helveticus* JCM1120 and *Pediococcus pentosaceus* JCM5890. The bacterial cell powders were added to a fermentation mixture (16% skim milk+0.5% yeast extract+7% isomerized sugar) at a concentration of 0.01%, and the mixtures were sterilized at 95° C. for 90 minutes. The fermentation mixture (16% skim milk+0.5% yeast extract+7% isomerized sugar) was used as a control. *Lactobacillus acidophilus* JCM1132 was inoculated into each fermentation mixture at a concentration of 3%, and the mixture was cultured at 37° C. until the acidity reached 1.5%. The cultures were mixed with isomerized sugar to produce yogurt drinks with BRIX of 15%. The yogurt drinks were stored at 15° C., and the cells were counted on days 0, 7, 14, and 21. Furthermore, for the purpose of comparison of the acid producing ability, the acidity during fermentation was determined with time 0, 24, 48, 72, and 96 hours after storage.

The effect of addition of the dead cells on acid production by *Lactobacillus acidophilus* is shown in FIG. 3, while the effect of addition of the dead cells on viability of *Lactobacillus acidophilus* is shown in FIG. 4. The results reveal that, as shown in FIG. 3, acid production is improved in all the samples to which the dead cells were added. Moreover, as shown in FIG. 4, changes in the numbers of bacterial cells during storage of the products show that viability is remarkably improved in all the samples to which the dead cells were added as compared with the control.

Example 3

In production of a fermented butter obtained by fermenting using three bacterial strains of *Lactococcus lactis* subsp. *lactis* ATCC19435, *Lactococcus lactis* subsp. *cremoris* ATCC19257, and *Lactococcus lactis* subsp. *diacetylactis* ATCC11007, an acidic buttermilk containing cells of the above-mentioned starter bacteria was obtained as a by-product. The acidic buttermilk was mixed in skim milk at a concentration of 4%, and the mixture was sterilized, concentrated, and spray-dried to prepare an skim milk containing acidic buttermilk that contains the dead cells, which is an agent for enhancing growth and improving viability of a lactic acid bacterium of the present invention.

The acidic buttermilk-containing skim milk (16%) that contains the dead cells was mixed with isomerized sugar (7%) to prepare a fermentation mixture, and the mixture was sterilized at 95° C. for 90 minutes. As a control, skim milk (16%) was mixed with isomerized sugar (7%) to prepare a fermentation mixture. *Lactobacillus casei* ATCC334 was inoculated into the respective fermentation mixtures at a concentration of 0.5% and then cultured at 37° C. until the acidity reached 2.1%. The resultant cultures were mixed with isomerized sugar to prepare yogurt drinks with BRIX of 15%. The yogurt drinks were stored at 15° C., and the cells were counted on days 0, 7, 14, and 21 after storage. Moreover, for the purpose of comparison of the acid producing ability, the acidity during fermentation was determined with time 0, 24, 48, 72, and 96 hours after storage.

FIG. 5 illustrates the effect of addition of acidic buttermilk containing the dead cells on acid production by Lactobacillus casei, and FIG. 6 illustrates the effect of addition of acidic buttermilk containing the dead cells on viability of Lactobacillus casei. The results reveal that, as shown in FIG. 5, acid production is slightly improved in the sample to which the acidic buttermilk containing the dead cells was added. Furthermore, as shown in FIG. 6, changes in the numbers of bacterial cells during storage of the products show that viability is remarkably improved in the sample to which the acidic buttermilk containing the dead cells was added as compared with the control.

Comparative Example 1

The buttermilk obtained as a by-product of butter was mixed with skim milk at a concentration of 4%, and the mixture was sterilized, concentrated, and then spray-dried to prepare a buttermilk-containing skim milk. A conventional butter production method has no fermentation process, so that the buttermilk produced as a by-product contains no bacterial cell.

The buttermilk-containing skim milk (16%) was mixed with isomerized sugar (7%) to prepare a fermentation mixture, and the mixture was sterilized at 95° C. for 90 minutes. As a control, skim milk (16%) was mixed with isomerized sugar (7%) to prepare a fermentation mixture. *Lactobacillus casei* ATCC334 was inoculated into the respective fermentation mixtures at a concentration of 0.5% and cultured at 37° C. until the acidity reached 2.1%. The resultant cultures were mixed with isomerized sugar to prepare yogurt drinks with BRIX of 15%, respectively. The yogurt drinks were stored at 15° C., and the cells were counted on days 0, 7, 14, and 21 after storage. Moreover, for the purpose of comparison of the acid producing ability, the acidity during fermentation was determined with time 0, 24, 48, 72, and 96 hours after storage. FIG. 7 illustrates the effect of addition of the buttermilk on acid production by *Lactobacillus casei*, and FIG. 8 illustrates the effect of addition of the buttermilk on viability of *Lactobacillus casei*.

The results reveal that, as shown in FIG. 7, acid production is slightly improved in the sample to which the buttermilk was added. Furthermore, as shown in FIG. 8, changes in the numbers of bacterial cells during storage of the products show that the number of bacterial cells decreases in the sample to which the buttermilk was added as well as the control.

Example 4

The bacterial cell powder of the present invention was prepared in the same manner as in Example 1.

The acid producing ability test and viability test was conducted using the bacterial cell powder. The bacterial cell powder was added to skim milk at a concentration of 0.007% to prepare a dead cell-containing skim milk as an agent for enhancing growth and improving viability of a lactic acid bacterium of the present invention. The dead cell-containing skim milk (16%) was mixed with isomerized sugar (7%) to prepare a fermentation mixture, and the mixture was sterilized at 95° C. for 90 minutes. As a control, skim milk (16%) was mixed with isomerized sugar (7%) to prepare a fermentation mixture. *Lactobacillus casei* ATCC334 was inoculated into the respective fermentation mixtures at a concentration of 0.5% and cultured at 37° C. until the acidity reached 2.1%. The resultant cultures were mixed with isomerized sugar to prepare yogurt drinks with BRIX of 15%.

The yogurt drinks were stored at 15° C., and the cells were counted on days 0, 7, 14, and 21 after storage. The results reveal that the skim milk to which the bacterial cell powder was added is improved on the acid production and remarkably improved on the viability as compared with skim milk containing no additive as a control.

Figure 1:
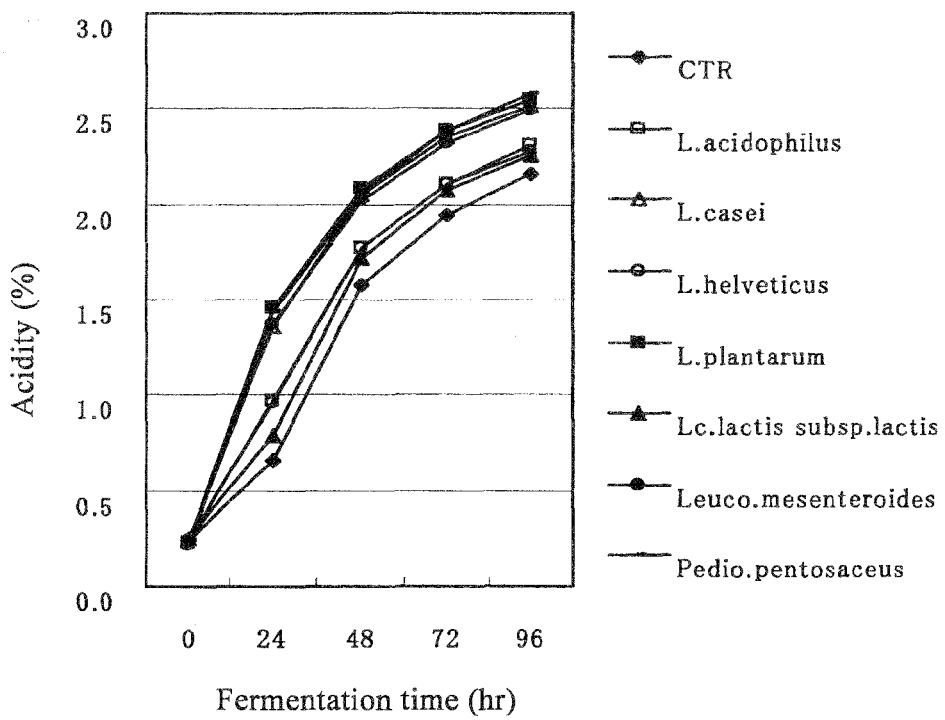
FIG. 1 illustrates the effect of addition of dead cells on acid production by *Lactobacillus casei* (Example 1).
Figure 2:
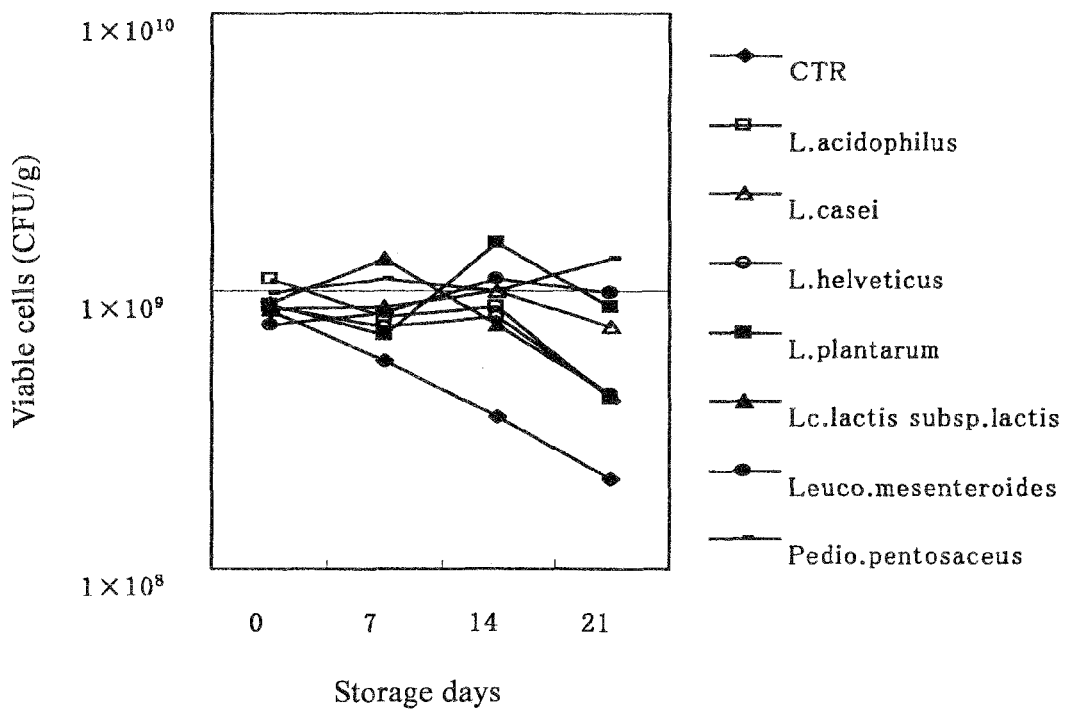
FIG. 2 illustrates the effect of addition of dead cells on viability of *Lactobacillus casei* (Example 1).
Figure 3:
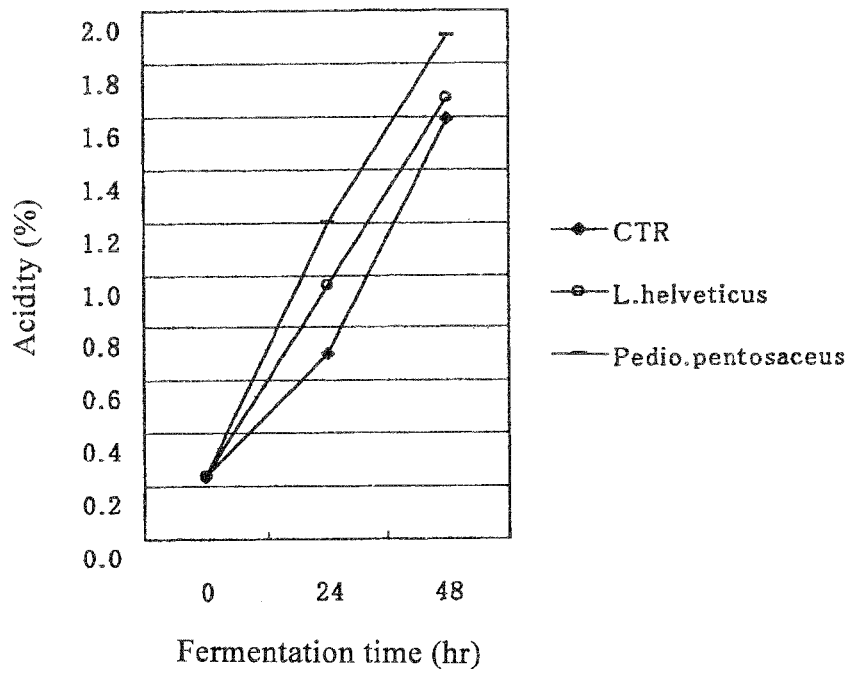
FIG. 3 illustrates the effect of addition of dead cells on acid production by *Lactobacillus acidophilus* (Example 2).
Figure 4:
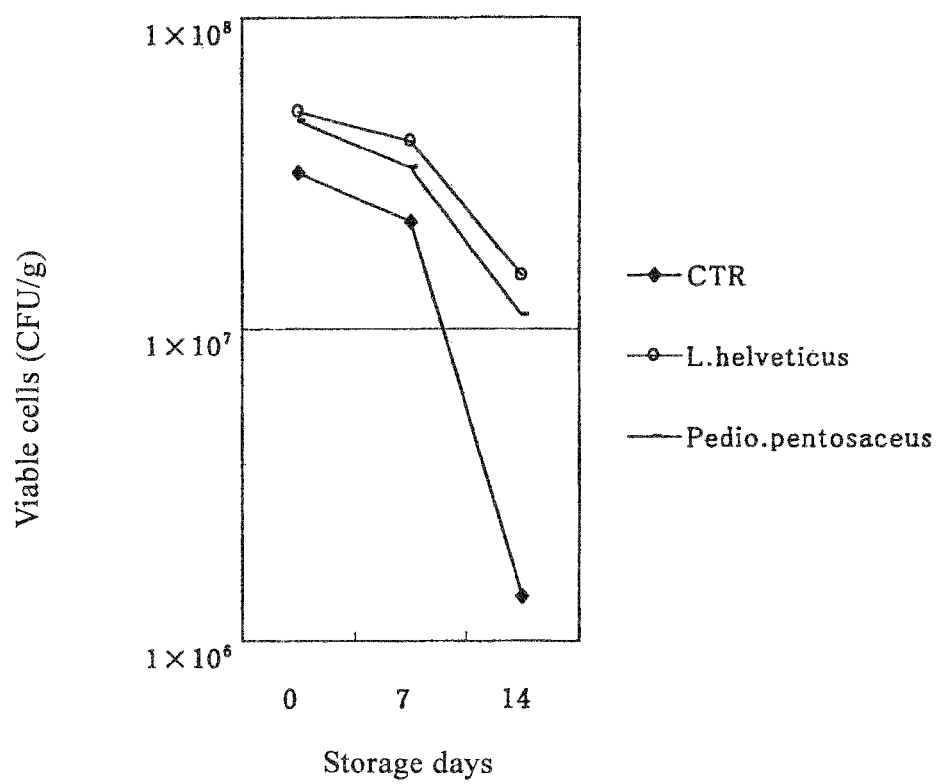
FIG. 4 illustrates the effect of addition of dead cells on viability of *Lactobacillus acidophilus* (Example 2).
Figure 5:
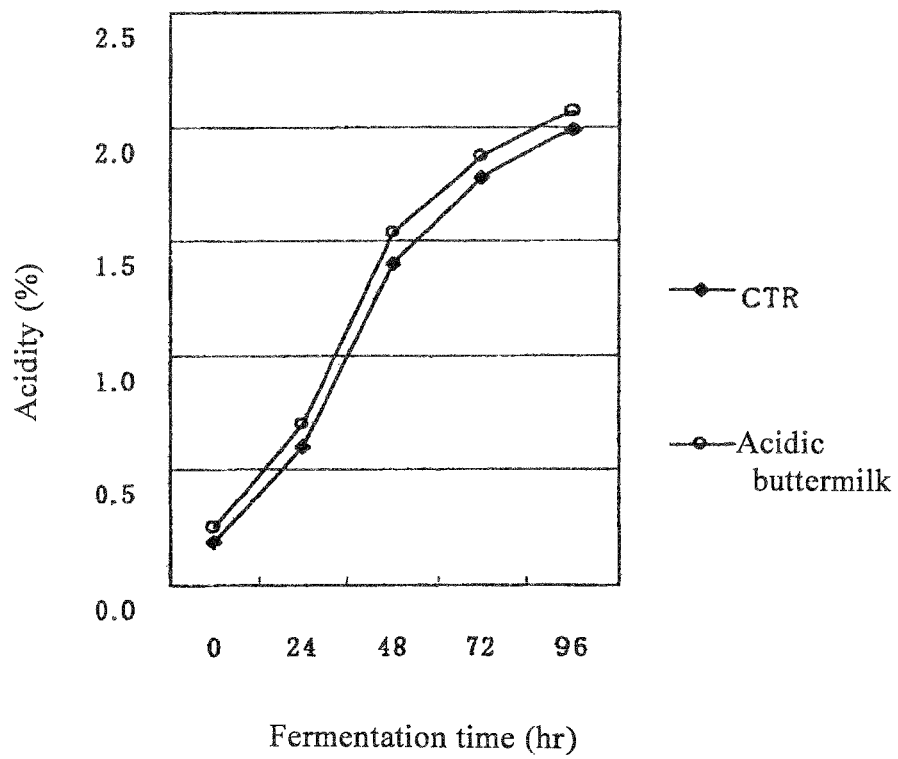
FIG. 5 illustrates the effect of addition of acidic buttermilk containing dead cells on acid production by *Lactobacillus casei* (Example 3).
Figure 6:
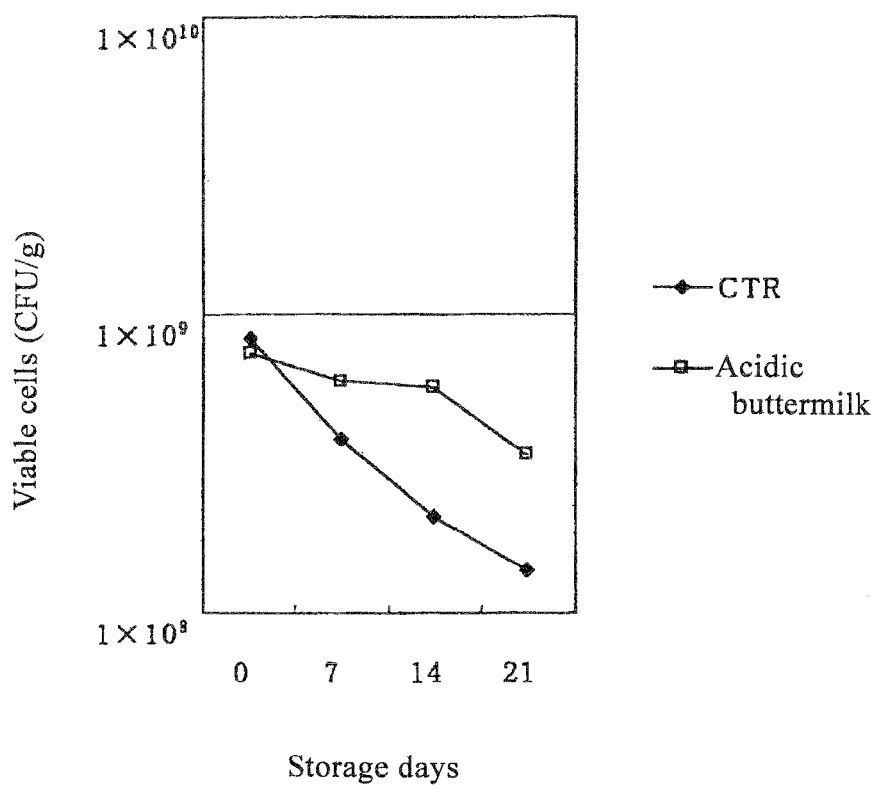
FIG. 6 illustrates the effect of addition of acidic buttermilk containing dead cells on viability of *Lactobacillus casei* (Example 3).
Figure 7:
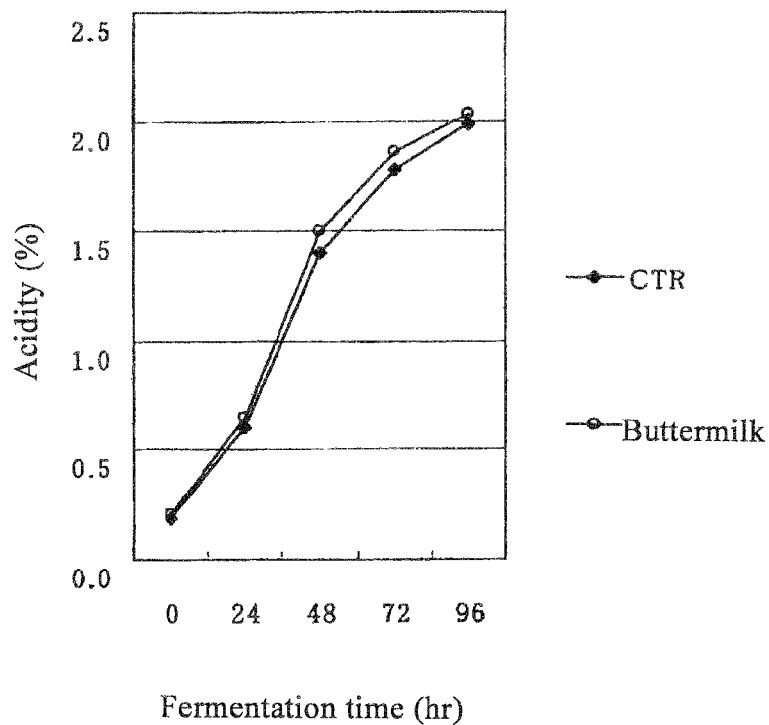
FIG. 7 illustrates the effect of addition of buttermilk on acid production by *Lactobacillus casei* (Comparative Example 1).
Figure 8:
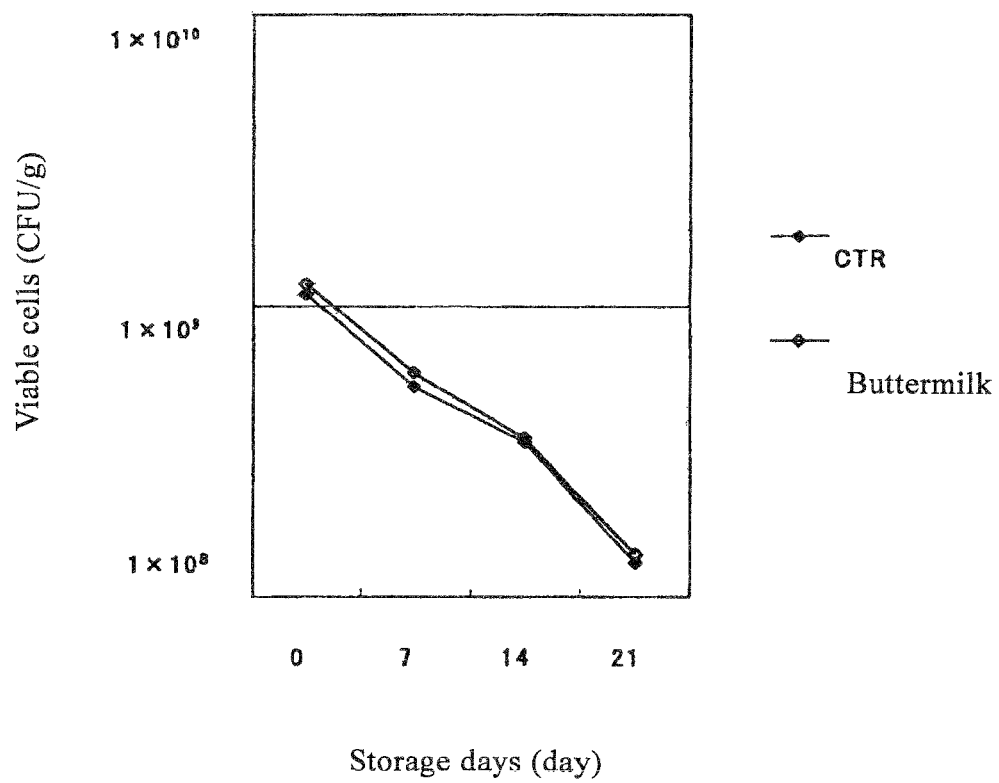
FIG. 8 illustrates the effect of addition of buttermilk on viability of *Lactobacillus casei* (Comparative Example 1).

The invention claimed is:

1. A method of enhancing growth and improving viability of one or more live lactic acid bacteria in a fermented milk product without impairing its flavor comprising including in the fermented milk product containing the one or more live lactic acid bacteria a concentration in a range of 0.001 to 0.01 weight percent (wt %) of dead cells of the one or more live lactic acid bacteria to enhance the growth and increase the viability of the one or more live lactic acid bacteria in the fermented milk product.

2. The method of claim 1, wherein the dead cells are of one or more of *Lactobacillus, Pediococcus, Leuconostoc, Lactococcus, Streptococcus, Weissella* and *Enterococcus*.

3. The method of claim 1, wherein the fermented milk product is a food or a drink.

4. The method of claim 1, wherein the fermented milk product is selected from the group consisting of milk, buttermilk, yogurt and cheese.

5. The method of claim 1, wherein the dead cells of the lactic acid bacterium are prepared by a method comprising:
providing live cells of the one or more live lactic acid bacteria;
sterilizing the live cells to produce dead cells of the one or more live lactic acid bacteria and drying the dead cells to produce a dry powder of the dead cells.

6. The method of claim 1, wherein the one or more live lactic acid bacterium is selected from the group consisting of *Lactobacillus casei* and *Lactobacillus acidophilus*.

* * * * *